United States Patent [19]

Whitefield

[11] Patent Number: 5,817,675

[45] Date of Patent: Oct. 6, 1998

[54] COMPOSITIONS FOR THE TREATMENT OF PSORIASIS AND THEIR USE

[75] Inventor: Martin Whitefield, London, United Kingdom

[73] Assignee: Diomed Developments Limited, United Kingdom

[21] Appl. No.: 863,396

[22] Filed: May 27, 1997

Related U.S. Application Data

[63] Continuation of Ser. No. 268,440, Jun. 30, 1994, abandoned.

[30] Foreign Application Priority Data

Jul. 5, 1993 [GB] United Kingdom .................. 9313866

[51] Int. Cl.⁶ .................................................. A61K 31/47
[52] U.S. Cl. ........................ 514/312; 514/171; 514/180; 514/863
[58] Field of Search ................................... 514/171, 180, 514/312, 863

[56] References Cited

U.S. PATENT DOCUMENTS

| 3,944,668 | 3/1976 | Cleaver | 424/227 |
| 4,038,388 | 7/1977 | Cleaver | 424/227 |

FOREIGN PATENT DOCUMENTS

| 0 278 660 | 8/1988 | European Pat. Off. | A61K 7/00 |
| 643860 | 7/1950 | United Kingdom . | |
| 981144 | 1/1965 | United Kingdom . | |
| 2 076 285 | 12/1981 | United Kingdom . | |
| 2 076 286 | 12/1981 | United Kingdom . | |

OTHER PUBLICATIONS

Nordenberg et al, *Eur.J. Cancer*, vol. 26, No. 8, pp. 905–907 (1990).
Minnich et al, *Dermatology Nursing*, vol. 3, No. 1, pp. 25–28 (1991).
Gupta, *J. Pharmi. Sci.*, 71(5):585–7 (1982).
Chemical Abstracts, 97/133427 (1982); 88:55014 (1977); 84:169598 (1976).
"The Merck Manual" (11th Edition) Lyght et al., Merck, Sharp & Dohme Research Laboratories (1966) pp. 1431–1433.
"The Merck Index" (11th Ed.), Budavari et al. Merck and Co., Inc., Rahway, N.J., 1989, pp. 184,769,770, and 1153.
WPIDS Abstract, AN 81–89674d, 1981, B.W. Fisher et al.
WIPDS Abstract, AN 81–89673d, 1981, B.W. Fisher.

*Primary Examiner*—Kevin E. Weddington
*Assistant Examiner*—M. Moezie
*Attorney, Agent, or Firm*—Cushman Darby & Cushman IP Group of Pillsbury Madison & Sutro

[57] ABSTRACT

8-Hydroxyquinoline is useful in the topical treatment of inflammatory proliferative skin diseases, especially psoriasis. It should be applied from an essentially anhydrous vehicle.

15 Claims, No Drawings

COMPOSITIONS FOR THE TREATMENT OF PSORIASIS AND THEIR USE

This is a continuation of application Ser. No. 08/268,440, filed on Jun. 30, 1994, now abandoned.

This invention relates to compositions for the topical treatment of inflammatory proliferative skin diseases, especially psoriasis, and their manufacture and use.

Psoriasis is associated with the rapid turnover of skin cells (hyperproliferation) accompanied by a loss of differentiation so that silvery white scales form on the surface of the skin. Additionally, the capillaries become tortuous and dilated and an inflammatory reaction occurs, so that the skin reddens. The elevated silvery white scales on a contrasting red background produce the unsightly lesions characteristic of psoriasis.

A number of methods are used for the topical treatment of psoriasis, but none is entirely satisfactory. Historically, the earliest form of therapy involved the use of coal tar derivatives. These are sometimes effective but are extremely messy. Subsequently, the use of dithranol (1,8-dihydroxy-9-anthrone) was developed. This substance is very effective, but it causes irritation of the skin and staining both of the skin and adjacent materials, which are disadvantages especially in home treatment. Topical corticosteroids have also been used. Although these are clean and convenient to use, they are only suppressive in action and therefore only provide short term relief of symptoms. In addition, psoriasis treated with corticosteroids tends to relapse in a more resistant form, so that more aggressive therapy is later required.

The latest form of topical treatment of psoriasis is the use of synthetic Vitamin D derivatives. These derivatives are reasonably effective but have to be used in extremely low concentrations in order to avoid systemic calcitropic effects. Thus, it has been shown that increasing the concentration of the derivative in the composition above 0.005% w/w is liable to cause an increase in plasma calcium levels and, even at the 0.005% w/w level used in the marketed licensed product, there have been reports of increased plasma calcium levels. Such preparations moreover rarely clear the psoriasis, perhaps because of the very low strength used. Patients therefore have to continue treatment for extended periods which increases the risk of systemic side effects. Furthermore, a significant proportion of patients experience irritation and this restricts usage, particularly on delicate areas of the skin such as the face. Although it is not known for certain, the Vitamin D appears to alter calcium metabolism in the epidermal cells, which results in reduced cell proliferation and increased cell differentiation, leading to a correction of the abnormal pathophysiology of the epidermal cells and a return to normal skin growth and development.

We have now found that 8-hydroxyquinoline is effective in the treatment of psoriasis and other inflammatory proliferative skin diseases by topical application to the affected area of skin. More particularly, we have found that 8-hydroxyquinoline at a concentration of 0.25% in a simple ointment or gel has a rapid ameliorating effect on patients with psoriasis. It rapidly removes the scales on resistant patches of psoriasis, such as those which occur on the elbows and knees.

A possible explanation for the effectiveness of 8-hydroxyquinoline may be that it deprives the epidermal cells of the calcium they need for rapid proliferation by chelating the calcium and thus rendering it unavailable. However other calcium chelating agents are not effective against psoriasis. For example ethylene diamine tetracetic acid and its salts were tested in various formulations and found to have no clinical effect whatsoever. Similarly, other chelating agents, including penicillamine, glycine, dimercaprol, citric acid, and 5-chloro-7-iodo-8-hydroxyquinoline (the topical antiseptic sold under the registered Trade Mark "Vioform") were all found to have no beneficial effect in the topical treatment of psoriasis.

8-Hydroxyquinoline is a white or slightly off-white solid which is relatively insoluble in water but dissolves in many organic solvents. When dissolved in anhydrous ethanol at a concentration of 1% w/w, it produces a clear almost colourless solution. On addition of water, e.g. 20% of the total volume, the 8-hydroxyquinoline remains in solution but the colour changes to yellow. This implies that 8-hydroxyquinoline exists in different forms, depending on whether or not water is present, viz a yellow form in the presence of water and a colourless form under essentially anhydrous conditions.

Trials have been carried out with both aqueous systems (e.g. aqueous gels) and essentially anhydrous systems (e.g. ointments or anhydrous gels) and it has been found that only the essentially anhydrous systems are effective in the treatment of psoriasis. Small quantities of water, e.g. 3 to 4% by weight, can be present in the essentially anhydrous compositions without them becoming inactive, but the desired therapeutic effect is lost if more than a small amount of water is present. This loss of activity is associated with the development of the yellow colour shown by 8-hydroxyquinoline in the presence of water and the presence or absence of this yellow colour thus provides a convenient way of determining whether a composition contains too much water to be active. It is thus a very simple matter to determine by experiment how much water a particular formulation can tolerate before it becomes inactive.

Water is not the only substance capable of rendering 8-hydroxyquinoline unavailable and, in consequence, without useful therapeutic effect. More particularly, acids and bases render 8-hydroxyquinoline unavailable by either converting it into a salt or limiting its release by hydrogen bond formation. Also substances such as polyhydric alcohols, polyethylene glycol, polyethylene glycol ethers and esters and non-ionic surfactants in general prevent release of 8-hydroxyquinoline into the skin from the phase containing it. The presence of such substances in the compositions of the invention must therefore be avoided. It is believed that all such substances which render 8-hydroxyquinoline therapeutically unavailable have the property already noted of converting it into a yellow form, a colour change which is believed to be associated with disturbance of the intramolecular hydrogen bonding of the 8-hydroxyquinoline, believed to be a prerequisite for efficient dermatological availability. The compositions of the invention are thus white (colourless) rather than yellow (unless a yellow colouring agent is added).

The present invention accordingly provides a pharmaceutical composition for topical application comprising 8-hydroxyquinoline in free form dissolved in a pharmaceutically acceptable essentially anhydrous solvent. Such compositions preferably comprise from 0.01 to 5.0% by weight, more preferably from 0.1 to 1.0% by weight, most preferably 0.1 to 0.5% by weight, of 8-hydroxyquinoline. The essentially anhydrous solvent is preferably paraffin or another topically acceptable, oleophilic, and water-immiscible solvent. A mixture of white soft paraffin and isopropyl myristate has the required properties and is preferred.

The pharmaceutical composition may further comprise a lipid soluble antioxidant which is chemically inert towards 8-hydroxyquinoline to protect the 8-hydroxyquinoline from atmospheric oxidation.

The pharmaceutical compositions may also comprise a topical corticosteroid, for example, betamethasone valerate, hydrocortisone, or another corticosteroid known to be suitable for topical application, in an amount of 0.01 to 1.0% by weight. These compositions are useful for treating cases where there is excessive inflammation present.

These pharmaceutical compositions are preferably for use in the treatment of an inflammatory proliferative skin disease, especially psoriasis.

The present invention further provides 8-hydroxyquinoline in free form for use in the treatment of, and in the manufacture of a medicament for the treatment of, an inflammatory proliferative skin disease, especially psoriasis, and a method of treating an inflammatory skin disease, especially psoriasis, which comprises applying 8-hydroxyquinoline in free form to skin affected by such disease.

Although the present invention is primarily concerned with the treatment of psoriasis, it is within the scope of the invention to use 8-hydroxyquinoline in the treatment of other inflammatory skin conditions in which hyperproliferation or thickening occurs, e.g. chronic eczema/dermatitis.

While a simple ointment containing 8-hydroxyquinoline in white soft paraffin is (as noted above) effective in the present invention, it is desirable to reduce the greasiness of the formulation while retaining the 8-hydroxyquinoline in an essentially anhydrous oleophilic environment. To achieve this objective, the compositions of the invention may be provided in the form of an oil-in-water semi-solid emulsion, in which the 8-hydroxyquinoline is dissolved in the discontinuous oil phase. The aqueous phase of such compositions must have a substantially neutral pH to ensure that the partition of 8-hydroxyquinoline is strongly in favour of the oil phase. In these circumstances, even though the continuous phase is aqueous, the 8-hydroxyquinoline is present in an essentially anhydrous environment because of the very low solubility of water in the dispersed oily phase. Such a composition may contain over 50% of a dispersed oil phase in which the 8-hydroxyquinoline is dissolved. Although the lipid phase is preferably preponderantly white soft paraffin, chosen for its inertness and water immiscibility, a small amount of isopropyl myristate is preferably added to improve emolliency. In addition, since 8-hydroxyquinoline may be subject to atmospheric oxidation, a small concentration of an antioxidant, may be included. It is also preferable that the aqueous phase contains a preservative, preferably phenoxyethanol in an amount of 0 to 0.2% by weight. This is because the 8-hydroxyquinoline, which is itself an antiseptic, is held almost entirely in the lipid phase.

In an alternative embodiment of the invention, the 8-hydroxyquinoline is provided as a therapeutically active gel by dissolving in it in free form in an essentially anhydrous pharmaceutically acceptable solvent and gelling with a thickener. For example, ethanol may be used which forms a clear colourless gel on the addition of hydroxypropyl cellulose. A small proportion of a soluble inert lipid, such as isopropyl myristate may be added to reduce the drying effect of the alcohol. Again, a small concentration of an antioxidant may be added. The amount of thickener to be added is adjusted to produce a final formulation varying from a slightly viscous liquid, for application as a lotion, to a semi-solid gel.

The following examples illustrate the invention. Parts are by weight.

EXAMPLE 1

|  | Most Preferred Range | Range |
| --- | --- | --- |
| 8-hydroxyquinoline | 0.1, 0.25, 0.5 or 1.0 | 0.01–5.0 |
| White Soft Paraffin BP | 40.0 | 10–50 |
| Isopropyl Myristate BP | 10.0 | 0–30 |
| Cetostearyl Alcohol BP | 7.0 | 5–10 |
| Sodium Lauryl Sulphate BP | 1.0 | 0.5–2.0 |
| Phenoxyethanol BP | 0.1 | 0–0.2 |
| Purified Water BP to | 100.0 | |

The formulation is made as follows:
1. Melt together the White Soft Paraffin (40 parts), isopropyl myristate (10 parts) and Cetostearyl Alcohol (7 parts) by heating to 70° C.
2. Dissolve 8-hydroxyquinoline (0.5 parts) in the heated oily phase so obtained.
3. Boil water (41.35 parts) thoroughly to remove any dissolved oxygen and allow to cool to 70° C.
4. Dissolve Sodium Lauryl Sulphate (1 part) and Phenoxyethanol (0.1 part) in the water at 70° C.
5. Add the aqueous phase so obtained to the oily phase and homogenise continuously, avoiding aeration, allowing the mixture to cool until semi-solid, to produce an almost white cream.
6. Pack into aluminium collapsible tubes.

EXAMPLE 2

|  | Most Preferred Range | Range |
| --- | --- | --- |
| 8-hydroxyquinoline | 0.1, 0.25, 0.5 or 1.0 | 0.01–2.0 |
| Isopropyl myristate BP | 10.0 | 5–15 |
| Hydroxypropyl Cellulose* BP | 3.0 | 0.5–3.5 |
| Ethanol BP to | 100.0 | |

*Klucel HF, Aqualon

The formulation is made as follows:
1. Dissolve the 8-hydroxyquinoline in the alcohol.
2. Add the isopropyl myristate and mix well.
3. Warm to 50°–60° C.
4. Add the hydroxypropyl cellulose slowly with continuous mixing, avoiding aeration.
5. Allow to cool with occasional mixing to form a clear colourless gel.
6. Pack into a bottle or aluminium tube depending on the viscosity.

The preparation should be applied twice daily to the affected areas of psoriasis. For thin areas of psoriasis a concentration of 0.1% to 0.5% 8-hydroxyquinoline may be sufficient, while for the thicker areas a concentration of 0.5% or 1.0% 8-hydroxyquinoline may be required. The preparation is non-irritant, it produces no staining, and has no effect on systemic calcium levels. It has been shown to be at least as effective as Vitamin D derivatives in some subjects, and even more effective in others. 8-hydroxyquinoline is particularly useful in the treatment of resistant areas of psoriasis which may have to be treated for extended periods.

If desired, betamethasone valerate may be incorporated in the above formulations in a concentration of 0.1% by weight.

I claim:

1. A method of treating psoriasis which comprises applying an effective amount of 8-hydroxyquinoline in free form in an anhydrous solvent to skin affected by psoriasis.

2. A method according to claim 1 wherein said 8-hydroxyquinoline in free form is applied in solution in a pharmaceutically acceptable anhydrous solvent as an ointment or anhydrous gel.

3. A method according to claim 1 wherein 8-hydroxyquinoline is present in amount of from 0.01 to 5.0% by weight.

4. A method according to claim 3 wherein 8-hydroxyquinoline is present in an amount of from 0.1 to 1.0% by weight.

5. A method according to claim 2 wherein the said solvent is oleophilic and water-immiscible.

6. A method according to claim 5 wherein the said solvent comprises a mixture of white soft paraffin and isopropyl myristate.

7. A method according to claim 2 wherein said solution also comprises an antioxidant.

8. A method according to claim 2 wherein said solution also comprises a topical corticosteroid.

9. A method according to claim 8 wherein the said topical corticosteroid is betamethasone valerate in an amount of from 0.01 to 1.0% by weight.

10. A method according to claim 2 wherein the said solution of 8-hydroxyquinoline is dispersed in an aqueous phase which has a neutral pH.

11. A method according to claim 10 wherein the said aqueous phase contains an anionic dispersing agent.

12. A method according to claim 10 wherein 0 to 0.2% by weight of phenoxyethanol is dissolved in the aqueous phase.

13. A method according to claim 1, wherein said 8-hydroxyquinoline in free form is applied in the form of a gel in which said 8-hydroxyquinoline is dissolved in a pharmaceutically acceptable solvent gelled with a thickener, said gel containing no more than about 4% water by weight.

14. A method according to claim 13 wherein the said solvent is ethanol and the said thickener is hydroxypropylcellulose.

15. A method according to claim 1 wherein said 8 hydroxyquinoline is applied in the form of an oil-in-water semisolid emulsion, the 8-hydroxyquinoline being in the oil.

* * * * *